United States Patent [19]

Firth et al.

[11] Patent Number: 5,624,400
[45] Date of Patent: Apr. 29, 1997

[54] DISPOSABLE SELF-SHIELDING ASPIRATING SYRINGE

[75] Inventors: John R. Firth, Wilsonville, Oreg.; Anthony R. Perez, Pasadena, Calif.

[73] Assignee: Safety Syringes, Inc., Arcadia, Calif.

[21] Appl. No.: 467,625

[22] Filed: Jun. 6, 1995

Related U.S. Application Data

[63] Continuation-in-part of Ser. No. 104,182, Aug. 9, 1993, Pat. No. 5,437,647, which is a continuation-in-part of Ser. No. 783,825, Oct. 29, 1991, Pat. No. 5,279,581, which is a continuation-in-part of Ser. No. 581,734, Sep. 12, 1990, Pat. No. 5,108,378, which is a continuation-in-part of Ser. No. 521,243, May 9, 1990, abandoned.

[51] Int. Cl.$^6$ .................................. A61M 5/00
[52] U.S. Cl. .................. 604/110; 604/232; 604/198
[58] Field of Search ........................ 604/232, 110, 604/192, 198, 263, 207, 187, 218, 230

[56] References Cited

U.S. PATENT DOCUMENTS

| | | |
|---|---|---|
| 827,383 | 7/1906 | McElroy et al. . |
| 1,652,894 | 12/1927 | Gunther . |
| 1,921,034 | 8/1933 | LaMarche . |
| 2,432,605 | 12/1947 | Barach . |
| 2,571,653 | 10/1951 | Bastien . |
| 2,586,581 | 2/1952 | Tschischeck . |
| 2,895,474 | 7/1959 | Reznek . |
| 2,925,083 | 2/1960 | Craig . |
| 3,046,985 | 7/1962 | Saenz . |
| 3,878,846 | 4/1975 | Rimbaud . |
| 3,885,562 | 5/1975 | Lampkin . |
| 3,930,499 | 1/1976 | Rimbaud . |
| 3,943,927 | 3/1976 | Norgren . |
| 4,018,223 | 4/1977 | Ethington . |
| 4,048,997 | 9/1977 | Raghavachari et al. . |
| 4,171,699 | 10/1979 | Jones et al. . |
| 4,356,822 | 11/1982 | Winstead-Hall . |
| 4,425,120 | 1/1984 | Sampson et al. . |
| 4,573,976 | 3/1986 | Sampson et al. . |
| 4,592,744 | 6/1986 | Jagger et al. . |
| 4,601,711 | 7/1986 | Ashbury et al. . |
| 4,631,057 | 12/1986 | Mitchell . |
| 4,643,199 | 2/1987 | Jennings, Jr. et al. . |
| 4,655,751 | 4/1987 | Harbaugh . |
| 4,690,676 | 9/1987 | Moulding, Jr. et al. . |
| 4,723,943 | 2/1988 | Spencer . |
| 4,728,321 | 3/1988 | Chen . |
| 4,737,144 | 4/1988 | Choksi . |
| 4,738,663 | 4/1988 | Brogan . |
| 4,743,234 | 5/1988 | Leopoldi et al. . |
| 4,762,516 | 8/1988 | Luther et al. . |
| 4,767,413 | 8/1988 | Haber et al. . |
| 4,772,272 | 9/1988 | McFarland . |
| 4,795,443 | 1/1989 | Permenter et al. . |
| 4,801,295 | 1/1989 | Spencer . |
| 4,813,426 | 3/1989 | Haber et al. . |
| 4,832,696 | 5/1989 | Luther et al. . |
| 4,840,185 | 6/1989 | Hernandez . |
| 4,850,961 | 7/1989 | Wanderer et al. . |
| 4,850,994 | 7/1989 | Zerbst et al. . |
| 4,871,355 | 10/1989 | Kikkawa . |
| 4,878,902 | 11/1989 | Wanderer et al. . |
| 4,892,523 | 1/1990 | Haber et al. . |
| 4,898,590 | 2/1990 | Andors . |
| 4,900,310 | 2/1990 | Ogle, II . |
| 4,915,701 | 4/1990 | Halkyard . |
| 4,915,702 | 4/1990 | Haber . |
| 4,917,669 | 4/1990 | Bonaldo . |
| 4,935,016 | 6/1990 | Deleo . |
| 4,938,745 | 7/1990 | Sagstetter . |

(List continued on next page.)

*Primary Examiner*—John D. Yasko
*Attorney, Agent, or Firm*—Lyon & Lyon

[57] ABSTRACT

There is disclosed herein a syringe with a protector case which holds a carpule and permits the injection of fluid contained in the carpule into the patient. The syringe is molded of plastic or other suitable material which is sterilizable. The device comprises several parts including a body, protector case, needle, needle cap, plug, plunger and harpoon. The harpoon can be integrally molded on the plunger. The major components of the device preferably are molded from a suitable plastic and may be clear or of a color like or similar to a surgical glove.

5 Claims, 13 Drawing Sheets

U.S. PATENT DOCUMENTS

| | | |
|---|---|---|
| 4,946,446 | 8/1990 | Vadher . |
| 4,946,447 | 8/1990 | Hardcastle et al. . |
| 4,957,490 | 9/1990 | Byrne et al. . |
| 4,974,603 | 12/1990 | Jacobs . |
| 4,990,141 | 2/1991 | Byrne et al. . |
| 5,002,537 | 3/1991 | Hoffman et al. . |
| 5,007,903 | 4/1991 | Ellard . |
| 5,013,305 | 5/1991 | Opie et al. . |
| 5,030,209 | 7/1991 | Wanderer et al. . |
| 5,045,066 | 9/1991 | Scheuble et al. . |
| 5,057,087 | 10/1991 | Harmon . |
| 5,059,185 | 10/1991 | Ryan . |
| 5,067,490 | 11/1991 | Haber . |
| 5,067,945 | 11/1991 | Ryan et al. . |
| 5,069,225 | 12/1991 | Okamura . |
| 5,070,884 | 12/1991 | Columbus et al. . |
| 5,070,885 | 12/1991 | Bonaldo . |
| 5,085,639 | 2/1992 | Ryan . |
| 5,086,780 | 2/1992 | Schmitt . |
| 5,088,982 | 2/1992 | Ryan . |
| 5,088,988 | 2/1992 | Talonn et al. . |
| 5,104,386 | 4/1992 | Alzain . |
| 5,108,376 | 4/1992 | Bonaldo . |
| 5,112,307 | 5/1992 | Haber et al. . |
| 5,116,319 | 5/1992 | van den Haak . |
| 5,120,311 | 6/1992 | Sagestetter et al. . |
| 5,131,405 | 7/1992 | Burns . |
| 5,137,521 | 8/1992 | Wilkins . |
| 5,154,699 | 10/1992 | Ryan . |
| 5,163,917 | 11/1992 | Huefner et al. . |
| 5,219,339 | 6/1993 | Saito . |
| 5,259,841 | 11/1993 | Hohendorfer et al. . |
| 5,266,072 | 11/1993 | Utterberg et al. . |
| 5,279,581 | 1/1994 | Firth et al. . |
| 5,330,438 | 7/1994 | Gollobin et al. . |

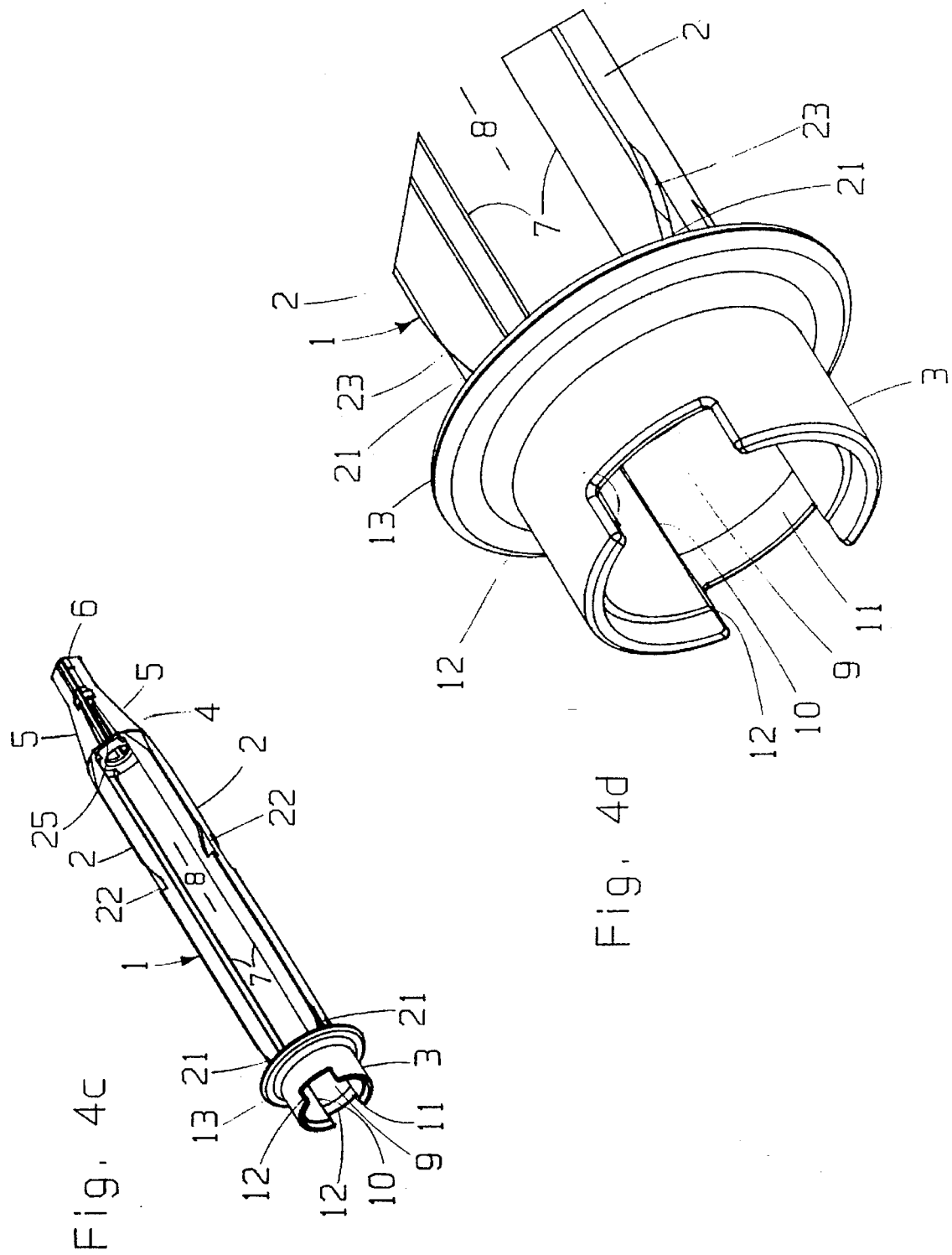

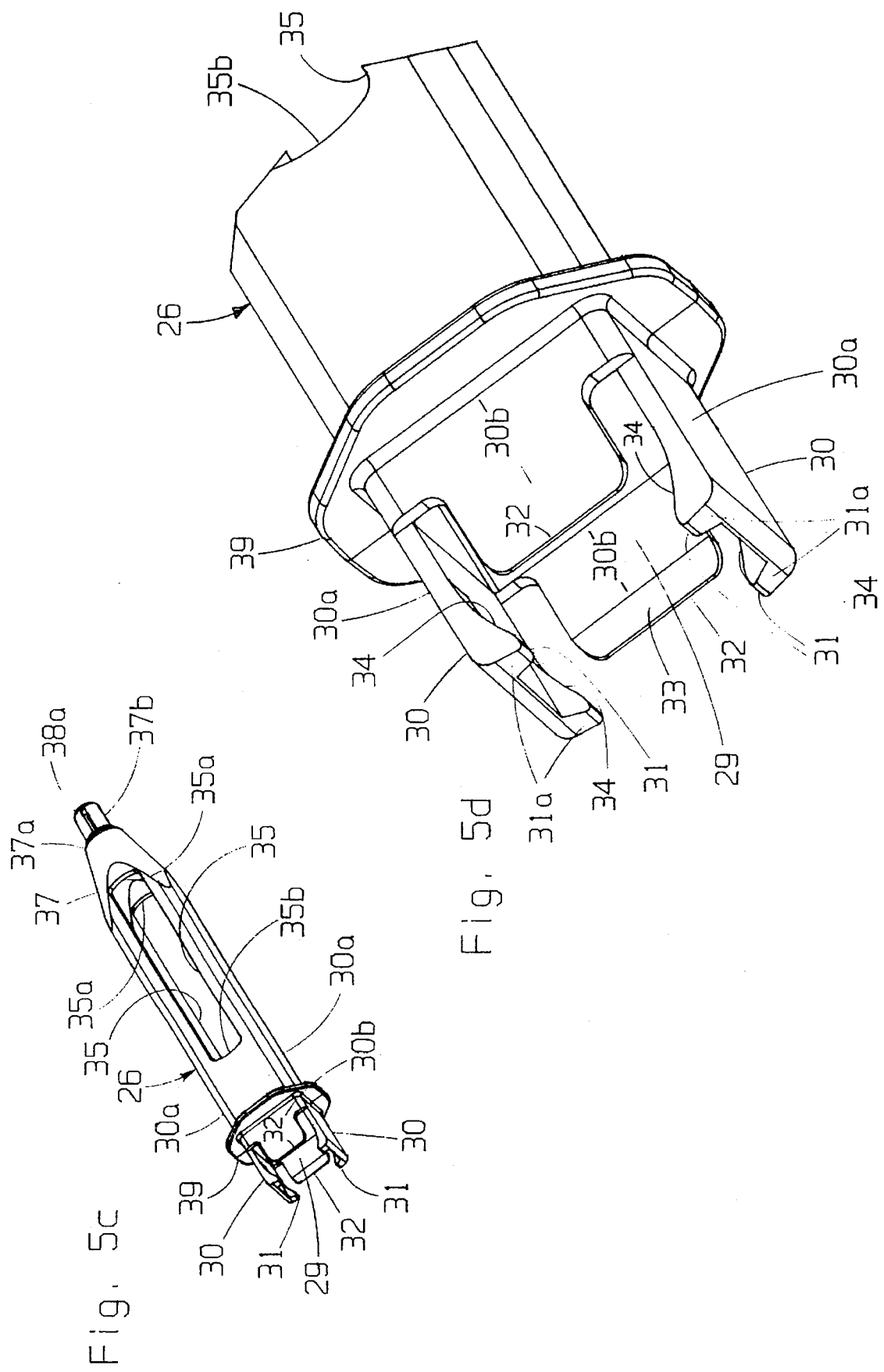

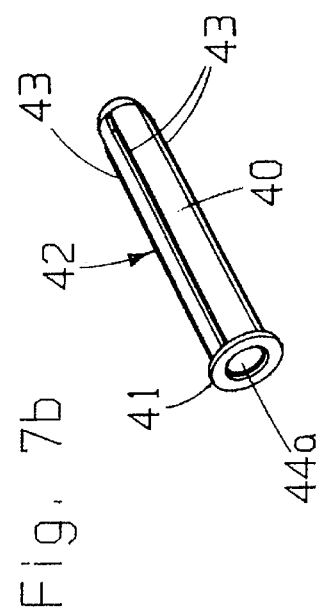
Fig. 7a
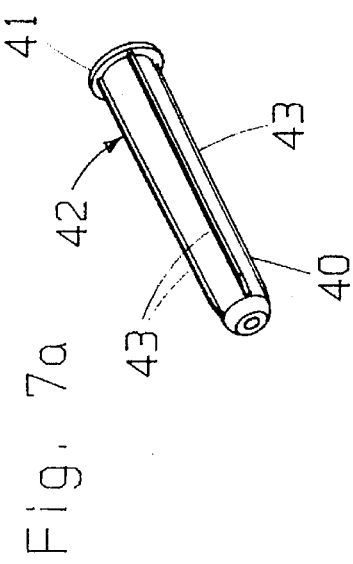
Fig. 7b
Fig. 6
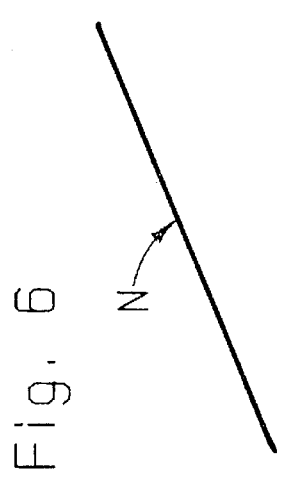
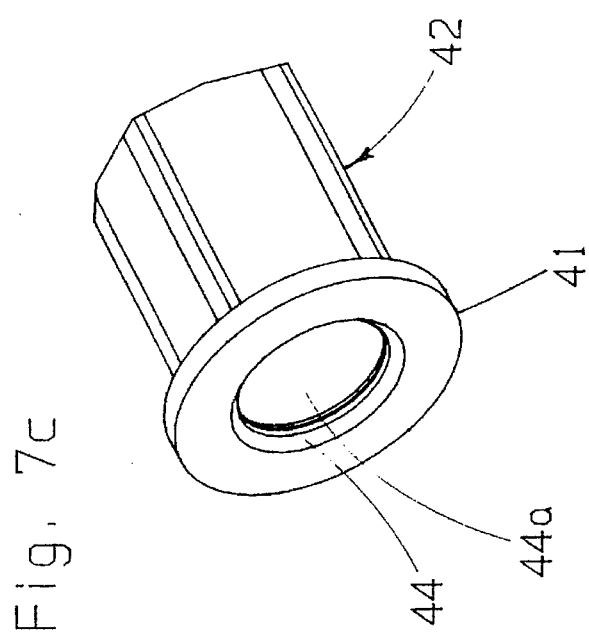
Fig. 7c

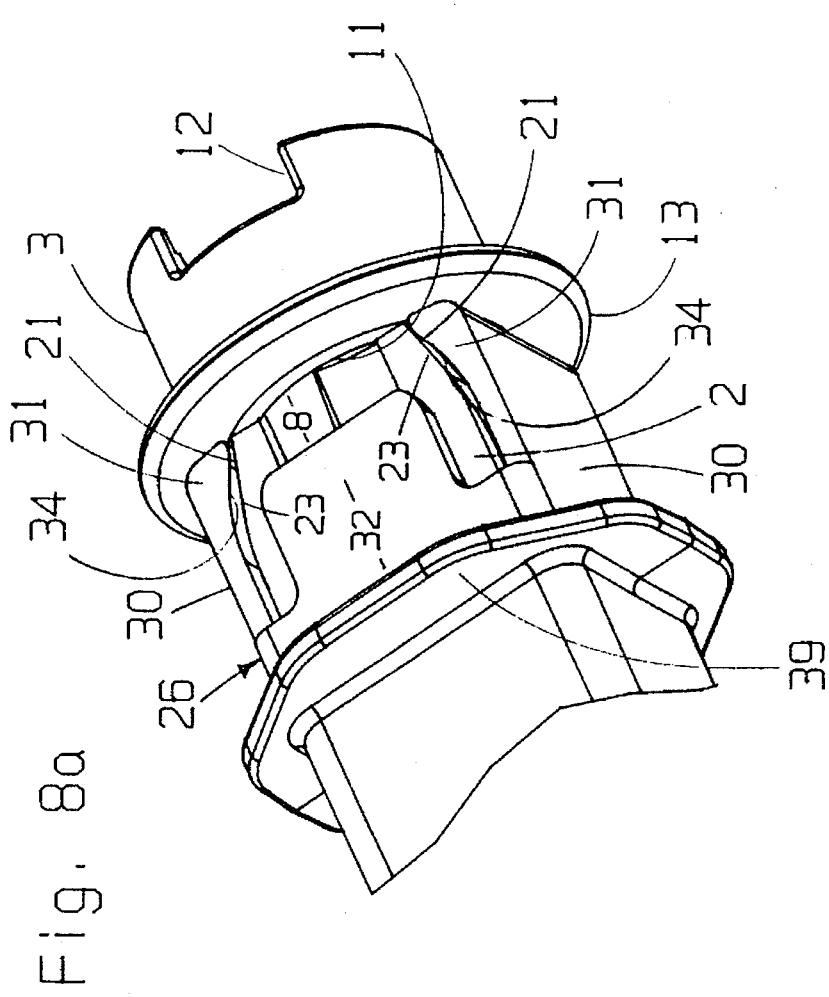
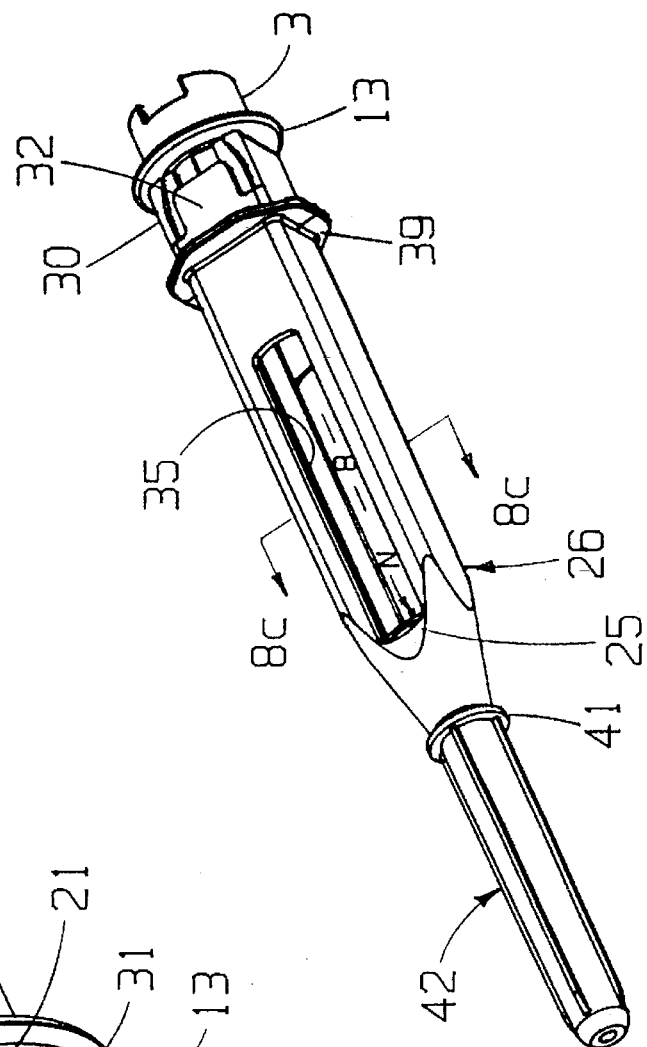
Fig. 8a
Fig. 8b

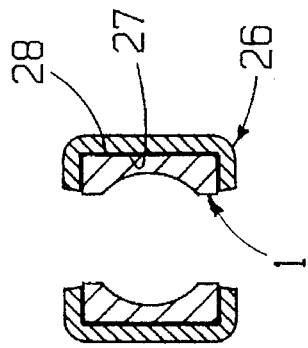
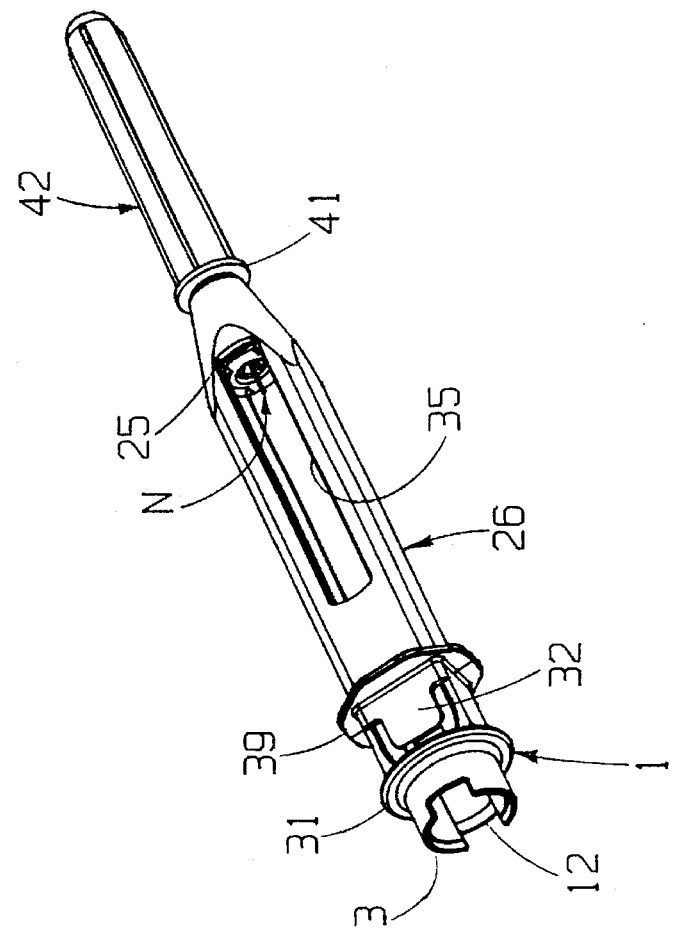
Fig. 8c
Fig. 8d

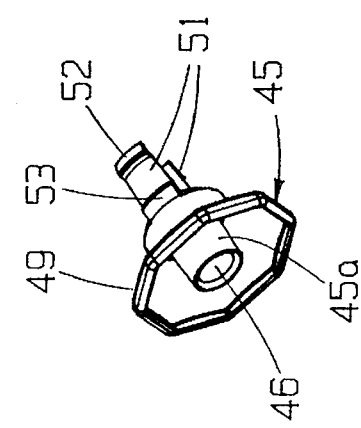
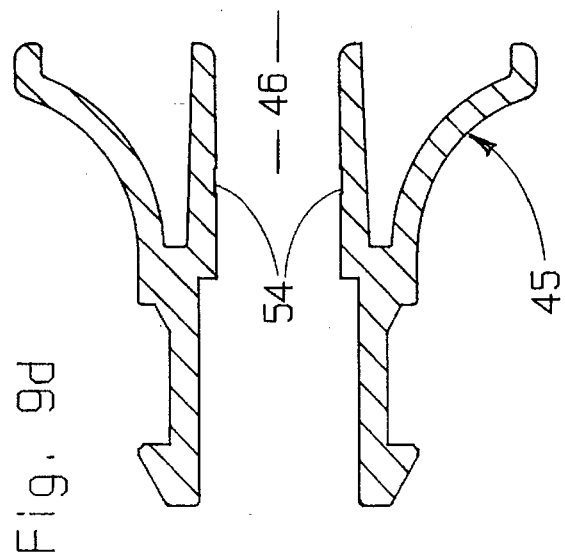
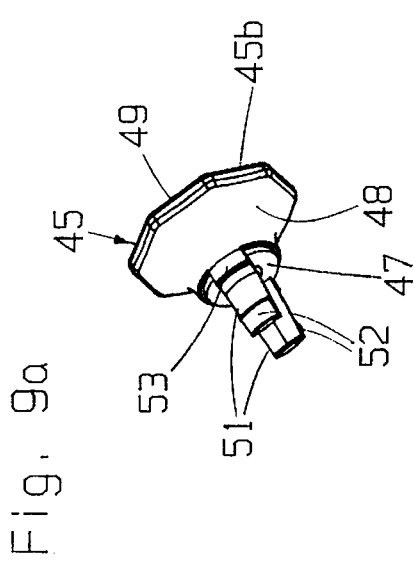
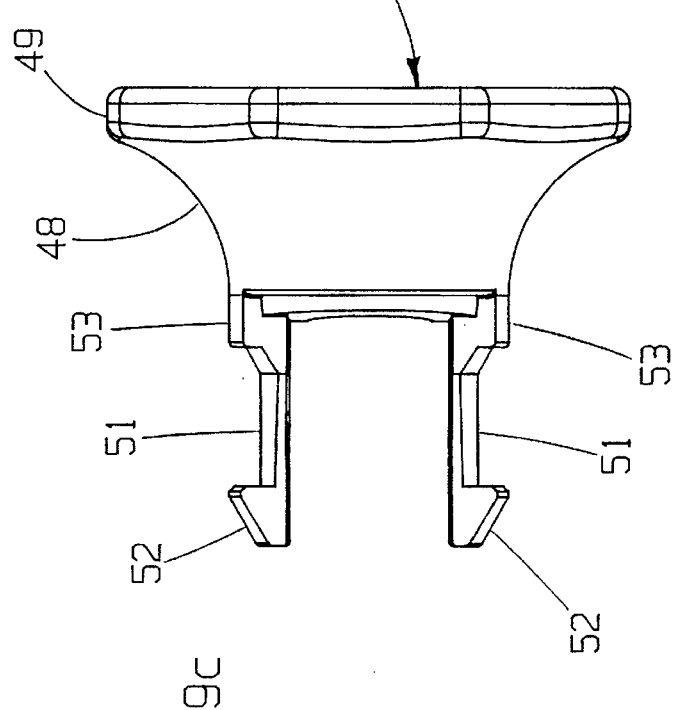

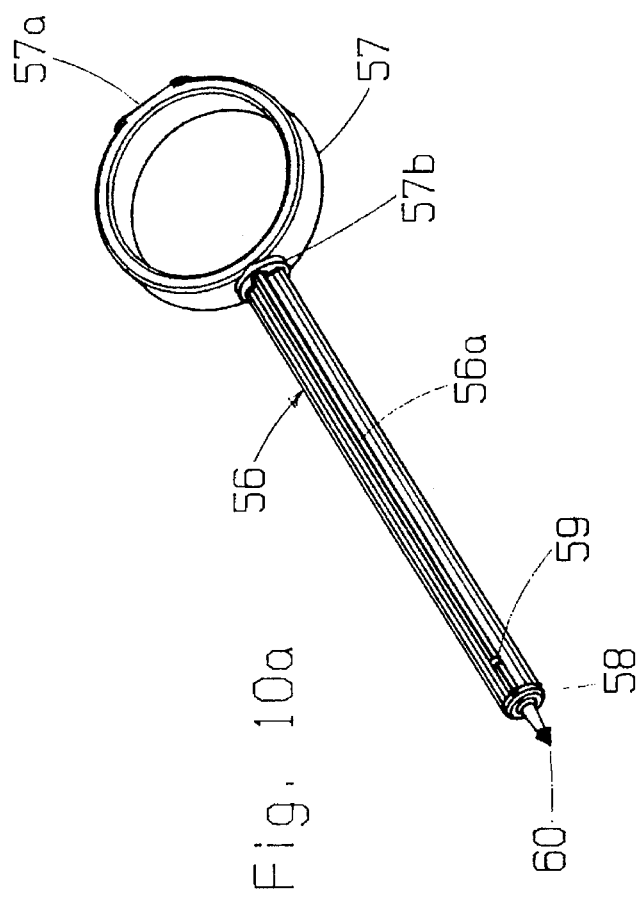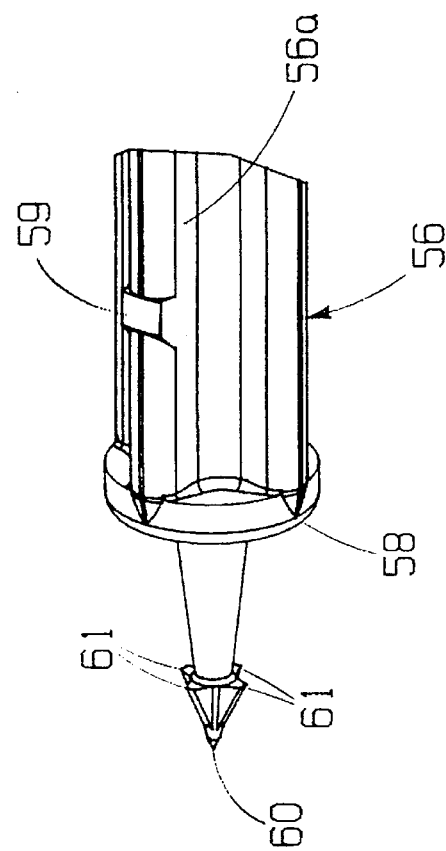

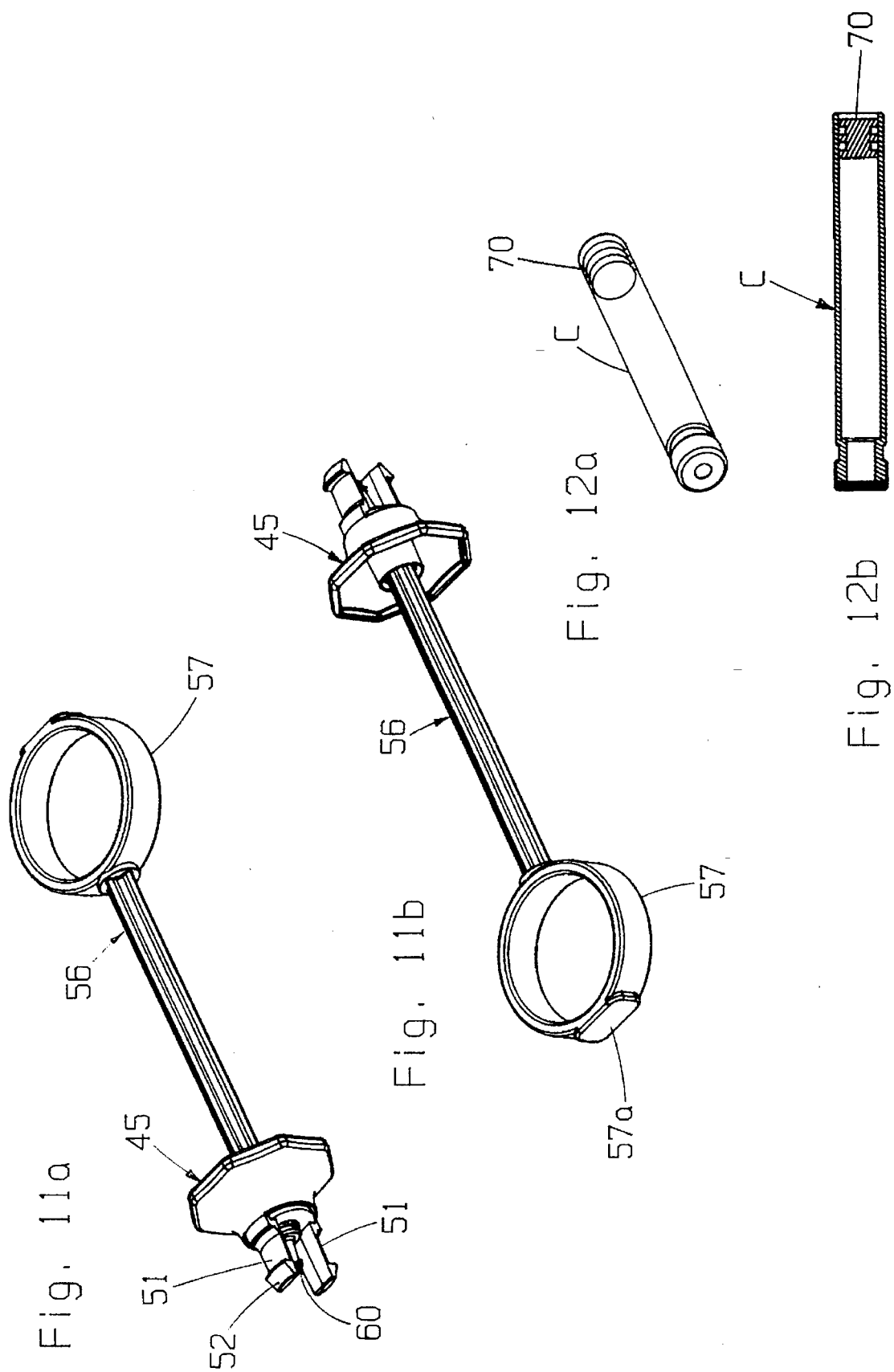

DISPOSABLE SELF-SHIELDING ASPIRATING SYRINGE

This is a continuation-in-part of application Ser. No. 08/104,182, filed on Aug. 9, 1993 now U.S. Pat. No. 5,437,647 which is a continuation-in-part of application Ser. No. 07/783,825 filed Oct. 29, 1991, now U.S. Pat. No. 5,279,581, which is a continuation-in-part of application Ser. No. 07/581,734 filed Sep. 12, 1990, now U.S. Pat. No. 5,108,378 which was a CIP of application Ser. No. 07/521,243 filed on May 9, 1990, now abandoned, by two of the applicants herein.

BACKGROUND OF THE INVENTION

The increasing threat of AIDS has generated a rapid development of methods for preventing the spread of communicable diseases from the inadvertent reuse of needle devices, accidental needlestick injuries suffered by medical and dental practitioners, and ineffective sterilization of reusable devices. To be effective, the devices employed must be simple to manufacture and easy to use. Our U.S. Pat. No. 5,108,378 discloses a syringe having a rectangular body cross-section which permits the use of a protector case of matching interior cross section. Parent application Ser. No. 0/104,182 describes the application of many of the features of the above patent to the design of an aspirating syringe of the type in common use by dentists for the administering of local anesthesia and in a hospital environment for the administering of controlled substances. The present application describes significant modifications to the features of the aspirating syringe which make it more effective for its intended purpose.

Numerous attempts have been tried to solve the problems noted above with respect to aspirating syringes. Examples of prior art devices are found in the disclosures of the following United States Patents:

U.S. Pat. No. 2,925,083 discloses a hood for concealing and guarding the needle of a syringe which may be easily retracted when the needle is inside the patients mouth.

U.S. Pat. No. 3,046,985 discloses a sleeve adapter which conceals the needle and applies pressure to the gum tissue.

U.S. Pat. Nos. 3,878,846 and 3,930,499 disclose a dental type syringe with a disposable body and case and a reusable finger grip and plunger. The case provides a sterile cover for the body and attached needle prior to use. The reusable finger grip allows the distance between the flanges of the finger grip to be adjusted.

U.S. Pat. No. 4,772,272 discloses an attachment for a reusable dental syringe which incorporates a sheath as part of the disposable needle assembly.

U.S. Pat. No. 4,915,701 discloses a reusable shield for attachment to a reusable dental syringe with a needle disconnect means to enable disconnecting the needle with the shield in place.

U.S. Pat. No. 4,957,490 shows an injection device having a system for retracting a needle into the body using rearward motion of a plunger.

U.S. Pat. No. 4,990,141 discloses a disposable syringe for use with a cartridge and having an elongated needle mount on the front of the body with a shield over the elongated mount.

U.S. Pat. No. 5,104,386 discloses a new design of reusable, dental type syringe having a spring actuated, semicircular shield.

U.S. Pat. No. 5,112,307 discloses a reusable dental syringe with a slidable needle carrier. The needle carrier and needle are retracted into the body section by means of the plunger.

U.S. Pat. No. 5,116,319 discloses a disposable syringe with a system for retracting the needle into the body cavity by means of the plunger.

U.S. Pat. No. 5,163,917 discloses a separate add-on sheath for use with a standard reusable aspirating syringe.

SUMMARY OF THE INVENTION

The present invention provides a syringe with a protector case which holds a glass cartridge and permits the injection of the fluid contained in the cartridge into the patient. The syringe is molded of plastic or other suitable material which is sterilizable. The device comprises six parts including a body, protector case, needle, needle cap, plug, and plunger. The major components of the device preferably are molded from a suitable plastic and may be clear or of a color like or similar to a surgical glove.

The device is normally provided to the practitioner in two assemblies. The body, protector case, needle, and needle cap make up the first assembly. The plug and plunger make up the second assembly.

The protector case is assembled by the manufacturer with the case retracted over the body and the needle attached to the body and extending through an opening in the protector case. The needle is covered by the needle cap which is removably attached to the needle hub on the end of the body. The body and case have a rectangular cross section.

A harpoon is molded as an integral part of the plunger and the plunger is inserted through the center tube of the plug with the harpoon positioned between locking fingers on the plug. The plunger is held in position by protrusions on vanes of the plunger which interact with indentations in the bore of the plug to maintain a desired position during handling, packaging, and assembly of the two sub-assemblies by the user.

The two assemblies are packaged together in a sealed container and sterilized.

The user removes the first assembly from the package and inserts a selected medicine cartridge into the open end of the body. The second assembly is then positioned with the locking fingers of the plug engaging slots in the end of the body and is pushed forward until the locking fingers clear the end of the slots and engage the interior surface of a finger grip on the body. The cartridge has the usual rubber stopper, and the plunger is driven rapidly forward by the hand of the user, or by striking on a hard surface, to engage the harpoon in the rubber stopper of the cartridge in a conventional manner. The needle cap is then removed and the syringe is ready for use. The engagement of the harpoon with the cartridge rubber stopper permits the user to aspirate fluid from the patient by retracting the rubber stopper and thereby to determine if the needle has punctured a blood vessel. Once the plunger is driven forward, the protrusions on the plunger vanes limit the rearward travel of the plunger during aspiration to prevent the rubber stopper from being pulled free of the cartridge.

After use, the protector case is slid axially forward over the needle until detents engage pockets on the edges of the body. In this position the needle is completely covered obviating the need to recap the needle and protecting those handling the device during disposal. Since the device is not intended for reuse, there is no need to remove the contaminated needle nor to autoclave or otherwise resterilize the device.

The benefits of the invention are several, including the following:

3

1. The device is sterilized after packaging and used only once, ensuring the maximum protection for the patient and practitioner.

2. The device may be used with any medication available in cartridges of the appropriate size.

3. The rectangular cross section of the body and protector case permit maximum exposure of the cartridge for easy viewing of the cartridge during aspiration and injection while providing the necessary rigidity of the device.

4. The rectangular cross section of the body and protector case make possible the use of the simple and effective detent mechanism for securing the protector case over the needle after use.

5. The protector case and single use/disposable nature of the device make it unnecessary to recap or remove the needle from the syringe eliminating exposure to the contaminated needle.

6. The device, or at least selected portions thereof can be molded of a suitably colored plastic and the appearance and feel of the molded syringe are less threatening to the patient resulting in more patient comfort.

7. The harpoon design makes penetration of the cartridge rubber stopper more easy to accomplish and retraction of the rubber stopper for aspiration less likely to result in the harpoon pulling out.

8. The plug design makes the two assemblies very easy to put together and difficult to disassemble.

9. The plunger design incorporates the harpoon as an integrally molded part, reducing the cost of molding and assembly.

It is thus an object of the present invention to provide an improved syringe.

BRIEF DESCRIPTION OF THE DRAWINGS

FIGS. 4a, 4b, 4c, and 4d are perspective views of the body of the syringe.

FIGS. 5a, 5b, and 5c are perspective views of the protector case.

FIG. 6 is a perspective view of the needle.

FIGS. 7a, 7b, and 7c are perspective views of the needle cap.

FIGS. 8a, 8b, and 8d are perspective views of the body and protector case assembly showing in greater detail the manner in which the body and case are interconnected, and FIG. 8c is a cross-sectional view along a line 8c—8c of FIG. 8b.

FIGS. 9a and 9b are perspective views of a plug of a plunger assembly and FIG. 9c is an enlarged side view of the plug.

FIG. 9d is a cross section view of the plug.

FIG. 10a is a perspective view of a plunger.

FIG. 10b is an enlarged view of a harpoon end of the plunger.

4

FIGS. 11a and 11b are perspective views of the plunger and plug assembly.

FIG. 12a is a perspective view of a standard glass medicine cartridge, and FIG. 12b is a cross-section thereof.

DETAILED DESCRIPTION OF THE PREFERRED EMBODIMENT

Figure 1:
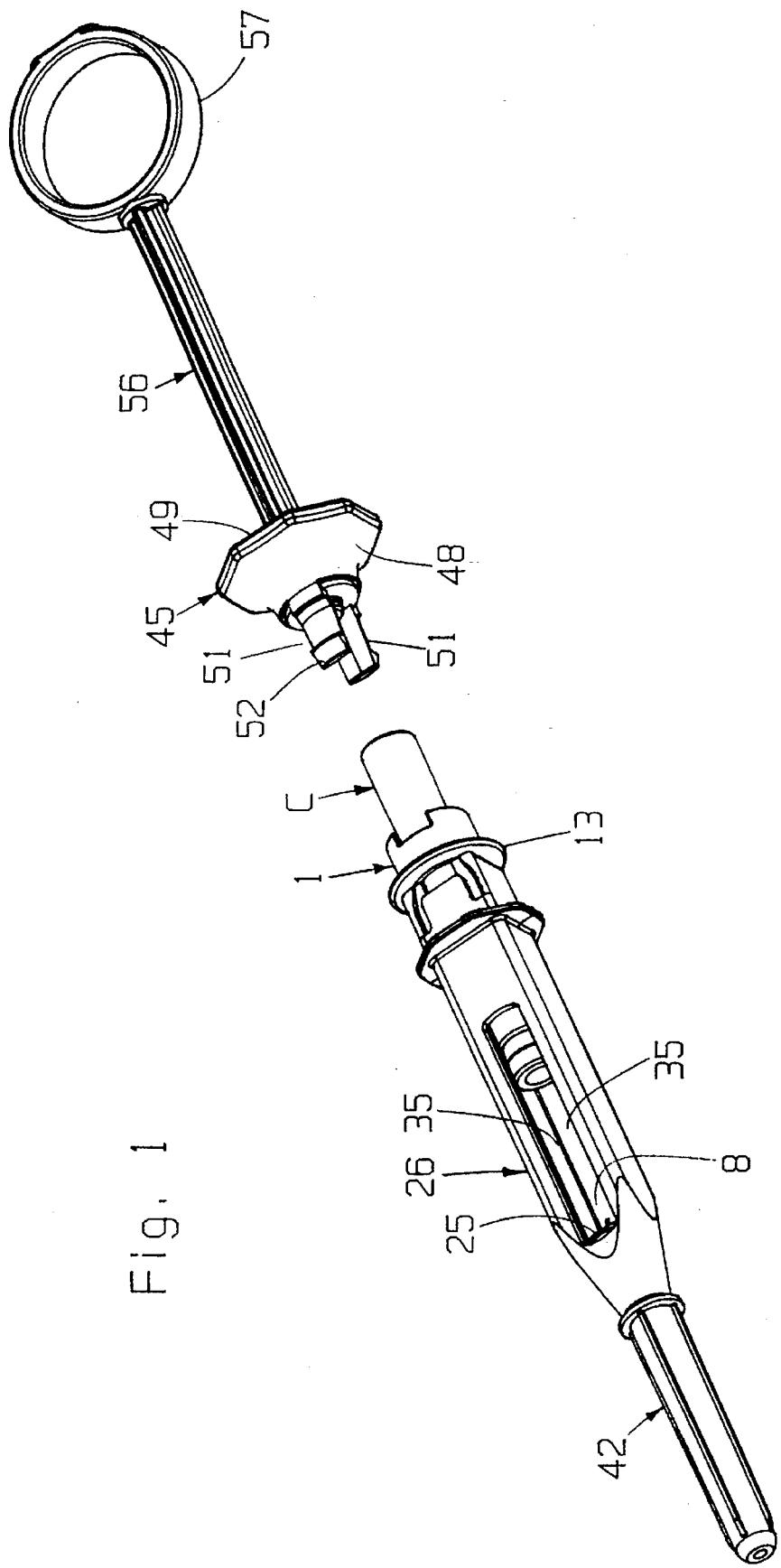
FIG. 1 is perspective view of a syringe of the present invention in its unassembled state, with a cartridge partially inserted, disclosing the interrelationship of the various parts.
Figure 2:
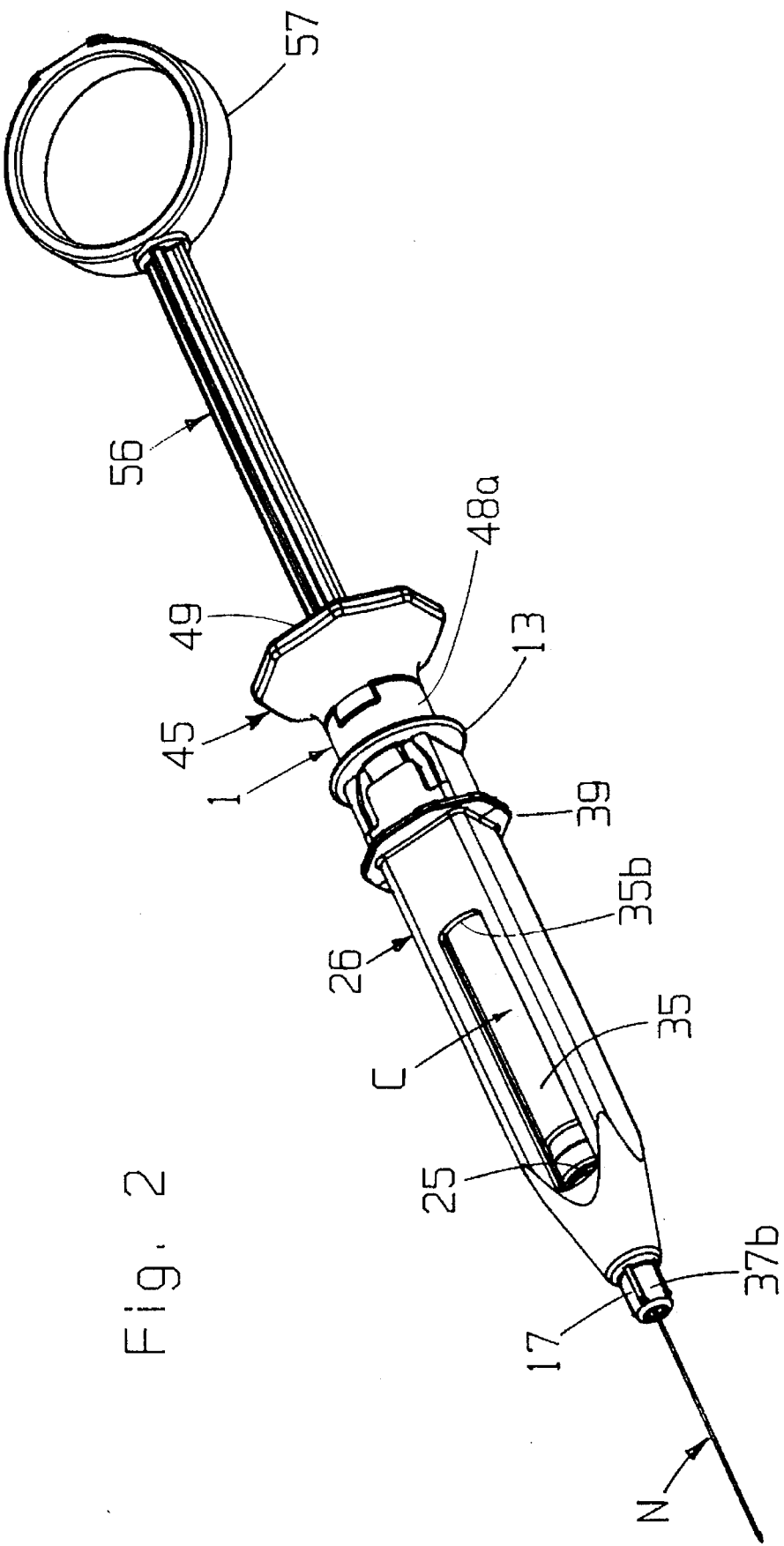
FIG. 2 is a similar perspective view of a syringe of the present invention in its assembled state, with a cartridge, with a protector case in the retracted position and a needle cap removed ready for use.
Figure 3:
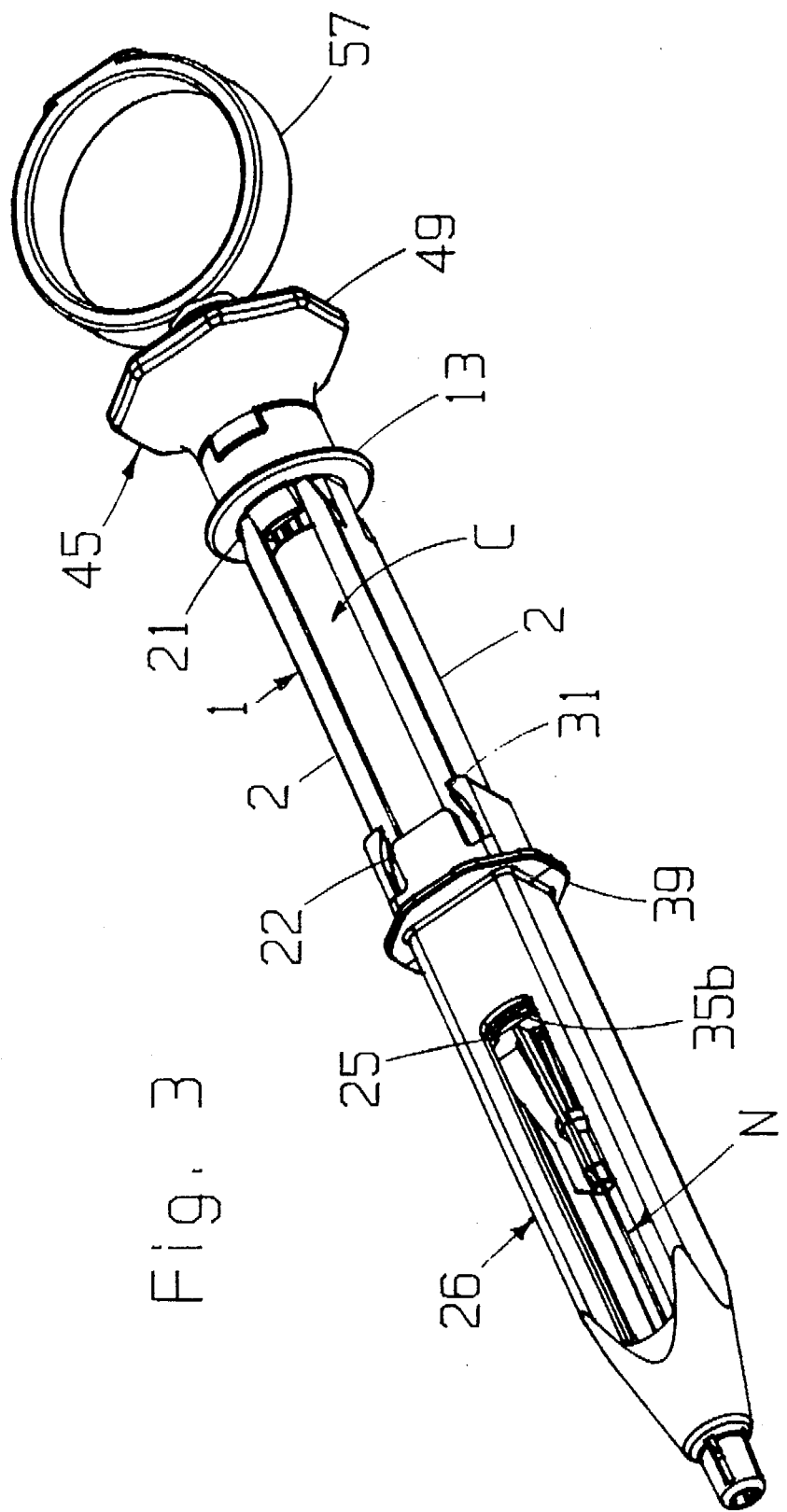
FIG. 3 is a similar perspective view of the syringe in its assembled state, with a cartridge, but with the protector case in an extended (guarded) position ready for disposal after use.

FIG. 1 illustrates the body 1 and case 26 of the first assembly with a standard medicine cartridge C partially inserted in a cavity 8 in the body, and the plug 45 and plunger 56 of the second assembly oriented for movement axially to complete assembly of the device. FIG. 2 shows the device fully assembled with a needle cap 42 (note FIG. 8b) removed to expose the needle, and FIG. 3 shows the device after use with the protector case 26 in the forward (guarded) position ready for disposal.

Referring to those Figures and particularly to the detailed drawings of FIGS. 4a, 4b, 4c, and 4d, the body 1 of the first assembly has two elongated side rails 2 with a finger grip collar 3 integrally molded at one end of the side rails 2, and an end wall 4, needle hub support vanes 5, and needle hub 6 integrally molded at the opposite end of the side rails. The side rails 2 have interior concave surfaces 7 which conform to the outer diameter of a standard glass medicine cartridge C (FIGS. 1 and 13) and form a cartridge cavity 8. The outer edges of the side rails define a rectangular cross-section 28 (see FIG. 8c) over which the protector case 26 is positioned. A circular opening 9 is provided through the finger grip collar 3 to permit passage of the cartridge C during loading of the cartridge into the cavity 8 of the body 1. Within the collar 3 are two tapered grooves 10 (FIG. 4d) running axially along the interior surfaces of the collar 3. At the anterior end of these grooves are located two tapered pockets 11 which extend radially outward through the finger grip collar 3 to form two notches 12. These pockets 11 are shaped to receive the ends of the two locking fingers 51 (FIG. 9) on the plug 45 when the second assembly is assembled to the first assembly as will be described subsequently. The notches 12 provide easy orientation of the plug 45 for proper assembly to the body. The finger grip collar 3 has a forward finger grip ring 13 extending radially outward at the forward end of the collar 3 to permit the body 1 to be gripped by the fingers of the user during aspiration (which involves rearward thrust on the plunger 56 and resultant rearward thrust on the body 1).

At the opposite end of the body 1, the end wall 4 forms the attachment between the two side rails 2 and provides the forward surface of the cartridge cavity 8. On the forward surface of the end wall 4, the four needle hub support vanes 5 are attached and extend radially outward from a core opening 14 and axially forward where they attach to the needle hub 6. The needle hub support vanes 5 have forward edges 17 (see FIG. 4a) parallel to the longitudinal axis of the body 1. These edges 17 interact with the needle cap 42 (FIG. 7) with the forward edges 17 engaging an interior bore 44a of the needle cap 42 to secure the cap 42 to the body 1. To further secure the needle cap 42 to the needle hub support vanes 5 there is a small radial protrusion 18 on the forward end of each edge 17 which has an interference fit with an interior bore 44a of the needle cap 42.

The structure of the end wall 4, support vanes 5, and needle hub 6 are configured to facilitate cooling of the mold core during molding of the body and minimization of the plastic volume in this area to improve heat transfer and manufacturing cycle times. The needle hub 6 has a circular opening 19 extending through the hub 6. This opening 19 forms an adhesive pocket which extends axially into the hub from the end away from the body. The needle N (FIG. 6) is attached so that it extends through the circular opening 19 with the interior end of the needle extending past the end wall 4 and into the cartridge cavity 8 to penetrate the forward end of the cartridge C as is known in the art. As an alternative, the hub 6 can be modified and have external threads to accommodate the present standard needle. This also involves modification of the end of the case 26 to accommodate the modified hub 6.

Turning now to the other end of the body 1, rear detent pockets 21 are located on the outer edges of the side rails 2, adjacent to the forward end of the finger grip ring 13. These pockets 21 accept detents 31 (FIG. 5c) of the protector case 26 when the protector case is in the rearward (unguarded) position (see FIG. 2). Similarly formed forward detent pockets 22 (note FIGS. 4b,4c) are located on the outer edges of the side rails 2 at a distance from the rear detent pockets 21 such that, when the protector case detents 31 are engaged in the forward detent pockets 22, the forward end of the protector case covers the outward end of the needle as shown in FIG. 3. The rear detent pockets 21 have front surfaces 23 which are angled from the plane normal to the axis of the body to permit the detents 31 on the protector case 26 to be readily disengaged from the rear detent pockets 21 by sliding the protector case 26 forward. The forward detent pockets 22 have rear surfaces 24 that are inclined at approximately 10 degrees from the plane normal to the longitudinal axis of the body 1 such that the outer edges of the rear surfaces 24 are closer to the needle end of the syringe body than are the inner edges. These rear surfaces 24 interact with the rear surfaces 31a of the detents 31 to prevent the protector case 26 from being moved in a rearward direction when the protector case detents 31 are engaged in the forward detent pockets 22.

The end wall 4 includes stop tabs 25 (FIG. 4a) which protrude from the top and bottom of the body 1 and interact with the ends of the windows 35 (FIGS. 1–3 and 5b–5c) in the top and bottom of the protector case 26 to limit the travel of the protector case 26 in the forward direction (note FIGS. 2, 8b and 8d).

Referring now to FIGS. 5a, 5b, 5c, 5d, and 8c, the protector case 26 comprises a tubular envelope with a rectangular internal cross-section which conforms to the rectangular external cross-section 28 of the body 1 as seen in FIG. 8c. The protector case has an open rear end 29 (FIGS. 5a, 5c, and 5d) with a pair of detent arms 30 and detents 31 integrally molded into the side wails 30a. Assembly tabs 32 with tapered inner edges 33 are integrally molded into the top and bottom walls 30b to facilitate the assembly of the protector case 26 over the stop tabs 25 (FIG. 4a) on the body 1. The detents 31 have sloped forward surfaces 34 (see FIG. 5d) which interact with the sloped forward surfaces 23 of the rear detent pockets 21 (FIG. 4d) of the body 1 to disengage the detents 31 from the rear detent pockets 21 of the body 1 when the protector case 26 is slid forward. Two elongated windows 35 are provided in the top and bottom walls 30b of the protector case 26 such that when the protector case 26 is in the rearward (unguarded) position as seen in FIG. 2, the forward edges 35a of the windows 35 are in close proximity to the forward surfaces of the stop tabs 25 and when the protector case 26 is in the forward (guarded) position as seen in FIG. 3, the rearward edges 35b of the windows 35 engage the rearward surfaces of the stop tabs 25 so that further forward motion of the protector case 26 is prevented by the engagement of the stop tabs 25 and rearward window edges 35b.

Figure 4A:
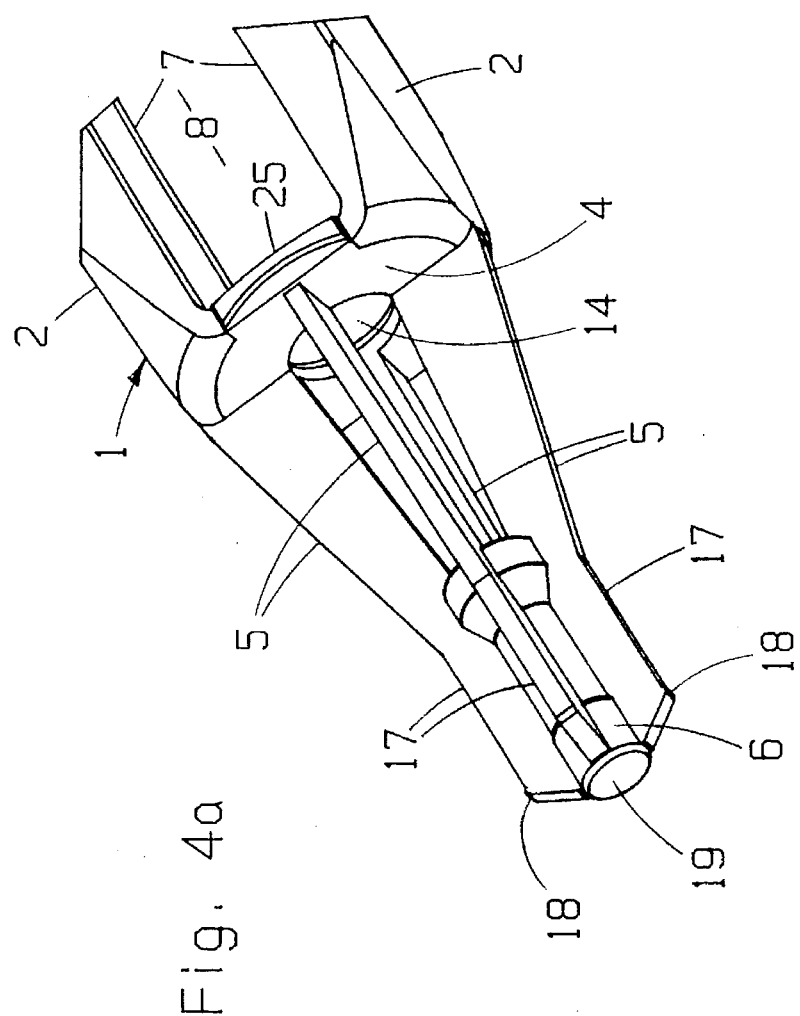
Figure 4B:
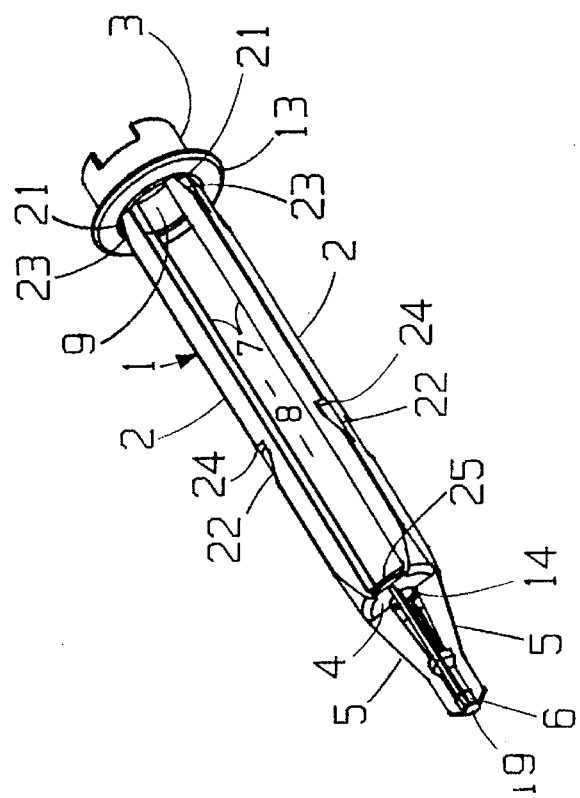
Figure 5A:
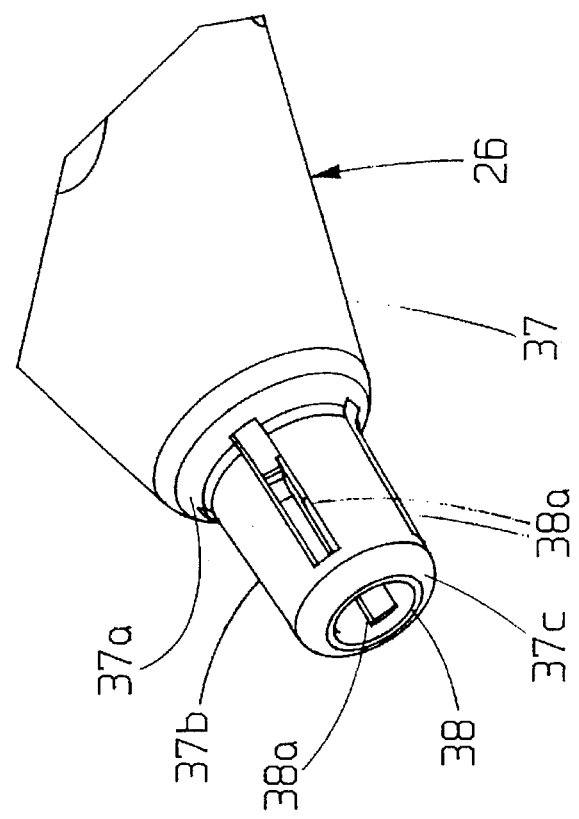
Figure 5B:
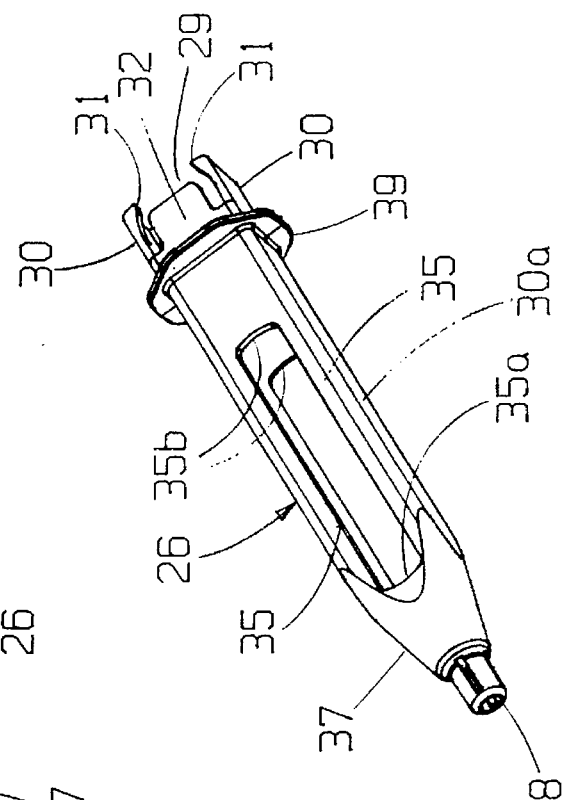

The forward end of the protector case is formed into a cone 37 which transitions from the rectangular section of the protector case 26 which covers the side rail area 2 of the body 1 to a smaller diameter 38 which covers the needle support vanes 5 (FIG. 4a). The forward end of the case 37 terminates in a collar 37a (FIG. 5a) to a sleeve 37b. The sleeve 37b has a smaller diameter than the edges 17 of the needle support vanes 5. The sleeve 37b has four slots 38a which permit the sleeve 37b to be drawn over the hub 6 with the edges 17 protruding through the slots 38a in the sleeve 37b. The sleeve 37b terminates in a solid annular ring 37c which ties the four segments of the sleeve together forming a stronger structure. This arrangement permits the cap 42 to be attached directly to the edges 17 of the body 1 while still enabling the end of the protector case 26 to have a small diameter 38. This arrangement also permits the needle cap 42 to be attached to the body 1 rather than the protector case 26 so as to prevent inadvertent actuation of the protector case 26 when the needle cap 42 is removed.

The protector case 26 has an actuator ring 39 molded to the protector case 26 in the area between the rear edges 35b of the windows 35 and the forward end of the detent arms 30. The ring 39 extends radially outward from the outer surface of the protector case 26 with the outer edges preferably defining an octagonal shape as best seen in FIG. 5d.

The needle N shown in FIG. 6 is in the form of a standard metal cannula having a hollow passageway through its length for the passage of fluids. The forward end is sharpened to permit penetration of the patient's tissue and the rear end is sharpened to permit penetration of the rubber membrane on the forward end of the medicine cartridge C in a conventional manner. The needle N is affixed to the needle hub 6 by adhesive during the manufacturing process. Alternatively, the hub 6 of the body 1 can be threaded to receive a standard needle.

The needle cap 42 as shown in FIGS. 7a, 7b, and 7c has a tapered section 40 with a ring 41 on its rear end. The tapered section 40 is closed at the forward end and has axial ribs 43 on its exterior surface. The ring 41 extends radially from the longitudinal axis and facilitates stripping and indexing in the manufacturing process. The inside surface 44a of the cap 42 is parallel to the longitudinal axis of the cap 42 for a distance approximately equal to the length of the forward edges 17 (FIG. 4a) of the needle support vanes 5. At the forward end of the forward edges there are slight protrusions 18 which have an interference fit with the inside surface 44a of the cap 42. These protrusions enhance the attachment of the needle cap 42 to the needle hub support vanes 5. On the rear end of the interior surface 44a there is a raised ring 44 of slightly smaller diameter which has an interference fit with the forward edges 17 (FIG. 4a) of the needle hub support vanes 5. This ring 44 enhances the attachment of the cap 42 to the needle hub support vanes 5 and also assists in stripping the molds in the manufacturing process.

These components are assembled into the first assembly as shown in FIGS. 8b and 8d and are shipped to the end-user with the protector case 26 in the rearward position as shown and the needle cap 42 in place over the needle. FIG. 8a particularly shows how the detents 31 of the protector case 26 fit within the detent pockets 21 of the body 1.

Referring to FIGS. 9a, 9b, 9c, and 9d, the plug 45 is shown and has an inner sleeve 45a with a cylindrical opening 46 passing through it. On the interior walls of the opening 46 there are two indentations 54 to receive protrusions 59 (see FIGS. 10a and 10b) on the plunger 56 to position the plunger 56 in the plug 45 during handling, packaging and shipping. An outer flared section 45b is molded to the forward end of the sleeve 45a at a face 47 and forms a rear finger grip 48. The outer edge 49 of this rear finger grip 48 is in the form of an octagonal section 49 which, in conjunction with the protector case actuation ring 39, which preferably has four or eight sides (octagonal as shown), and rectangular protector case section 26, substantially prevents rolling of the syringe when placed on a flat surface.

Locking fingers 51 are molded to the face 47 of the plug 45 and extend axially forward. Locking detents 52 are located at the ends of the locking fingers 51. At the face end of each locking finger 51 is a base section 53 which is of a form and shape required to fill the notches 12 (FIGS. 4c and 4d) in the finger grip collar 3 of the body 1 so that, when the plug 45 and body 1 are assembled, the finger grip area 48a (see FIG. 2) has a smooth, comfortable surface. The outer surfaces of the locking fingers 51 and locking detents 52 are equidistant from the longitudinal axis of the plug 45 which maintains more uniform wall thickness in the mating sections 10, 11, and 12 of the finger grip collar 3 of the body 1.

Referring to FIGS. 10a and 10b, the plunger 56 has an elongated column 56a of substantially cruciform or "+" cross section with a thumb ring 57 on the rearward end and an end cap 58 on the forward end. The thumb ring 57 has a flat surface 57a on the rearward end to facilitate striking the plunger 56 when setting the harpoon 60 in the cartridge C. A circular boss 57b is located at the joint between the plunger column 56a and the thumb ring 57 to strengthen the plunger and facilitate handling during assembly. Two protrusions 59 are located on the edges of the elongated column 56a near the forward end near the end cap 58. These protrusions 59 interact with the indentations 54 (FIG. 9d) in the bore 49 of the plug 45 to position the plunger 56 in the plug 45 during handling, packaging and shipping. These protrusions 59 also interact with the face 47 of the plug 45 after setting the harpoon to prevent the plunger 56 from being retracted far enough to pull the rubber stopper 70 out of the cartridge C during aspiration.

On the forward end of the plunger 56 there is a harpoon 60 integrally molded to the end cap 58. The harpoon 60 has four barbs 61 extending radially from the axis of the harpoon 60 and plunger 56. Molding the harpoon 56 directly to the plunger 56 results in a simpler mold for the plunger 56, eliminates the cost of a separate harpoon part, and eliminates the cost of assembly of the harpoon to the plunger.

Although the plug 45 can be designed with threads to engage similar threads on the body 1, the locking finger 51 arrangement is preferred. These fingers 51 are flexible so that the plug 45 and body 1 can be quickly and easily assembled by pushing the finger 51 end of the plug into the opening 9 (note FIG. 4d) of the body 1. The finger 51 structure also is simpler and cheaper to mold. A threaded connector between the plug 45 and body 1 would allow the two to be easily separated, which is undesirable; whereas, with the presently described construction with fingers 51, the two are not at all easy to separate. When the fingers 51 are snapped in place in the body 1 and subsequently the plunger 56 is pushed forward to push the harpoon 60 into the rubber stopper 70 of the cartridge C, it is very difficult to then remove the plug 45 from the body 1 because the plunger column 56a is positioned between and bears against the fingers 51 preventing them from flexing inward to thereby prevent the locking detents 52 from disengaging from the finger grip ring 13 on body 1. This provides an important safety feature as can be appreciated. Furthermore, the protrusions 59 (note FIGS. 10a and 10b) on the plunger column 56a preferably have a slightly larger diameter than the hole 46 in the plug 45 (FIG. 9b) to prevent the plunger 56 from being easily pulled out of the plug 45. If the plunger 56 is retracted from the plug 45 the harpoon 60 pulls the rubber stopper 70 of the cartridge C back between the fingers 51 and thus it would be necessary for the user to compress both the cartridge stopper 70 and the fingers 51 of the plug 45 in order to get the plug 45 loose from the body 1.

The plug 45 and plunger 56 are assembled into the second assembly, as shown in FIGS. 11a and 11b, and are shipped in this form with the first assembly. After use the entire syringe assembly, including the needle N, is disposed of.

Except for the needle, all of the above described components are injection molded using conventional techniques. The materials preferably used are plastics of the type used for sterilizable medical devices such as polypropylene, polycarbonate, styrene butadiene.

Another advantage, in addition to simplifying manufacture and providing a readily disposable syringe, in molding the syringe components (other than the needle) from plastic is that if the syringe components contact the skin of the patient, the syringe does not feel cold to the touch as with conventional metal aspirating dental syringes. Furthermore, and of particular importance, is the fact that the syringe components can be molded from a colored plastic or otherwise colored and, significantly, can be molded of a color which is the same as or similar to the color of surgical gloves (typically an ivory or almost or substantially white color). By providing this particular color, at least for the portions seen by a patient (i.e., the ring 57, plunger 56 and the plug 45), the color of the syringe blends into the color of the glove and becomes essentially an extension of the practitioner's hand and therefore appears to be less obtrusive or threatening to the patient. Also, any other color can be provided as desired, particularly in the event the color of surgical gloves is changed from the standard substantially white or ivory.

DESCRIPTION OF THE ASSEMBLY AND OPERATION OF THE PREFERRED EMBODIMENT

The syringe device of the present invention is assembled at the manufacturing facility into the two sub-assemblies as shown in FIGS. 8b and 11a. These sub-assemblies are placed together and sealed in a suitable container which provides a microbial barrier. The packaged devices are then sterilized by gamma radiation, or in any other recognized manner, and shipped to the end user either directly or through a distribution chain.

Immediately prior to use, the container is opened and the body sub-assembly shown in FIG. 8b is removed. The cartridge C of FIG. 12 containing the selected medication is next inserted into the cartridge cavity 8 as seen in FIG. 8b. The plug assembly of FIG. 11 is then removed and the locking fingers 51 are aligned with the notches 12 (see FIGS. 4d and 8d) in the finger grip ring 3 of the body 1. The plug 45 is pushed forward until the detents 52 of the locking fingers 51 engage the forward wall of the finger grip ring 13 of the body 1. As the locking fingers 51 move forward, the front ends of the locking fingers 51 push against the rear surface of the cartridge C forcing the cartridge forward over the rear end (see FIG. 8d) of the needle N which penetrates the standard rubber seal on the forward end of the cartridge C in a conventional manner.

The plunger 56 can then be forced sharply forward by striking the finger ring 57 with the palm of the hand of the user or against a hard surface in a conventional manner. This imbeds the harpoon 60 in the rubber stopper 70 with the barbs 61 engaged in the stopper 70.

The needle cap 42 can then be removed and the needle N inserted into the patient. The rubber stopper 70 of the cartridge C is then moved rearward by retracting the finger ring 57 of the plunger 56 to draw body fluid into the cartridge C (aspiration) in the usual way to determine if the needle N has penetrated a blood vessel and, if not, the plunger 56 is pushed forward to discharge the medication contained in the cartridge C into the patient.

After injection, the needle N is retracted from the patient. As the syringe is withdrawn the protector case 26 may be grasped with the free hand of the user and held as the syringe is moved away from the patient thus sliding the protector case 26 forward over the needle N and into the guarded position as shown in FIG. 3. Alternatively, the protector case 26 may be operated with one hand by moving the index and middle fingers forward between the rear of the protector case actuator ring 39 and the front of the finger grip ring 13 moving the thumb rearward in the ring 57 thereby drawing the body 1 rearward into the protector case 26. As the protector case 26 slides forward, the detents 31 engage the forward detent pockets 22 preventing subsequent rearward movement of the protector case 26. The stop tabs 25 and rear edges 35b of the windows 35 provide a positive stop when moving the protector case 26 forward to cover the needle N. The entire device is then disposed of without further exposure of the needle or other action required.

The improvements which are the particular subject of the present invention are:

A modified configuration of the plunger 56 which includes the molding of the harpoon 60 as an integral part of the plunger which eliminates a separate part, simplifies the mold configuration for the plunger, and eliminates a step in the assembly process.

A new design for the molded harpoon 60 which increases the force required to pull the plunger free of the rubber stopper 70 thus reducing the incidence of inadvertent release of the stopper 70 during aspiration.

Addition of protrusions 59 on the vanes 56a of the plunger 56 and undercuts 54 in the bore of the plug 45 which interact to create an improved method of positioning the plunger relative to the plug in the second assembly.

Positioning the protrusions 59 on the vanes 56a relative to the harpoon tip 60 to provide an interaction between the protrusions and the forward wall of the plug 45 at the exit of the bore 46 through the plug to prevent the plunger 56 from being easily retracted beyond the point of interference thus substantially reducing the likelihood of the rubber piston of the medicine cartridge C being pulled free of the cartridge during the aspiration process.

Addition of an annular ring 38 to the distal end of the protector case 26 to strengthen the structure without affecting the feature which permits the needle cap 42 to be attached to the body 1 rather than the protector case 26 so as to prevent inadvertent actuation of the protector case 26 when the needle cap 42 is removed.

Modification to the angle and shape of the detents 31 on the protector case 26 and the detent pockets 22 on the body 1 to reduce the force necessary to release the detents from the rear pockets and slide the protector case forward over the needle.

While embodiments of the present invention have been shown and described, various modifications may be made without departing from the scope of the present invention, and all such modifications and equivalents are intended to be covered.

What is claimed is:

1. A medical syringe for injecting medication into a human, comprising a syringe body, and a protector case movable with respect to the body to expose a needle connected to the body for injection and to cover the needle for disposal, the body having a cavity for receiving a medicine cartridge, the body having a first forward end to which the needle is attached and which needle also is capable of penetrating a cartridge for injecting medicine through the needle into a human, and the body having a second end into which a cartridge can be inserted, a protector case adapted to slidably fit on the body, and having a first open end through which a needle may extend and a second end, the case and the body have cooperating detents for facilitating placement of the case with respect to the body for uncovering and covering, respectively, an exposed end of the needle, and wherein the first open end of the case is substantially cylindrical with a plurality of radially disposed slots and wherein an outer area of the first open end thereof is in the shape of a solid annular ring, and a plunger assembly for cooperatively mating with the second end of the body and comprising a movable plunger which is movable with respect to the body for causing medicine from a cartridge to be administered through the needle, the plunger comprising a first end adapted to be manipulated by the user of the syringe and a second end adapted to be inserted into the body for engaging a stopper of a cartridge therein, the plunger being molded of plastic and the second end thereof having an integrally molded harpoon thereon which is adapted to engage and connect with a stopper of a cartridge disposed in the body.

2. A syringe as in claim 1 wherein the first end of the body for receiving a needle is tapered and includes a plurality of radially disposed fins adapted, when assembled with the case, to engage and extend through the slots in the first open end of the case.

3. A syringe as in claim 2 wherein the fins terminate in projections which are adapted to cooperatively mate with an open end of a needle cap.

4. A medical syringe for injecting medication into a human, comprising a syringe body, and a protector case movable with respect to the body to expose a needle connected to the body for injection and to cover the needle for disposal, the body having a cavity for receiving a medicine cartridge, the body having a first forward end to which the needle is attached and which needle also is capable of penetrating a cartridge for injecting medicine through the needle into a human, and the body having a second end into which a cartridge can be inserted, a protector case adapted to slidably fit on the body, and having a first open end through which a needle may extend and a second end, the case and the body have cooperating detents for facilitating placement of the case with respect to the body for uncovering and covering, respectively, an exposed end of the needle, and a plunger assembly for cooperatively mating with the second end of the body and comprising a movable plunger which is movable with respect to the body for causing medicine from a cartridge to be administered through the needle, the plunger comprising a first end adapted to be manipulated by the user of the syringe and a second end adapted to be inserted into the body, for engaging a stopper of a cartridge therein, the plunger being molded of plastic and the second end thereof having an integrally molded harpoon thereon which is adapted to engage and connect with a stopper of a cartridge disposed in the body, and wherein the plunger assembly further includes a plug through which the plunger extends and wherein the plug is adapted to couple with the second end of the body, the plunger including a plurality of radially disposed vanes having protrusions thereon for engaging undercut sections in a bore of the plug for facilitating positioning the plunger relative to the plug of the plunger assembly.

5. A medical syringe for injecting medication into a human, comprising a syringe body and a protector case movable with respect to the body to expose a needle for injection of medicine into a human and to cover the needle for disposal, and a plunger and plug assembly movable for causing medication to be injected into a human, the plunger and plug assembly comprising an elongated plunger and a plug which are adapted to be cooperatively reciprocally coupled together and the plug being adapted to couple and become affixed to an open end of the body which open end is adapted to receive a cartridge containing medicine, and the plunger having a first end adapted to be manipulated by the user and a second end having an integrally molded harpoon thereon adapted to be coupled with and become affixed to a movable stopper of the cartridge, and wherein the plunger has a pair of protrusions thereon and the plug has a bore with a pair of indentations wherein the protrusions interact with the indentations during handling, packaging and shipping of the plunger and plug, and the plug having a face which interacts with the protrusions of the plunger to limit the retraction of the plunger once the harpoon thereof becomes affixed to the stopper of the cartridge.

* * * * *